United States Patent
Pasqualoni et al.

(10) Patent No.: US 9,398,986 B2
(45) Date of Patent: Jul. 26, 2016

(54) PRE-FASTENED AND REFASTENABLE PANT-TYPE ABSORBENT SANITARY ARTICLE AND METHOD FOR MANUFACTURING THE SAME

(71) Applicant: Fameccanica.Data S.P.A., Pescara (IT)

(72) Inventors: Paolo Pasqualoni, Chieti (IT); Gabriele Sablone, Pescara (IT)

(73) Assignee: Fameccanica Data S.P.A., Pescara (IT)

( * ) Notice: Subject to any disclaimer, the term of this patent is extended or adjusted under 35 U.S.C. 154(b) by 0 days.

(21) Appl. No.: 14/395,030

(22) PCT Filed: Oct. 30, 2012

(86) PCT No.: PCT/IB2012/056006
§ 371 (c)(1),
(2) Date: Oct. 16, 2014

(87) PCT Pub. No.: WO2014/020382
PCT Pub. Date: Feb. 6, 2014

(65) Prior Publication Data
US 2015/0148767 A1    May 28, 2015

(30) Foreign Application Priority Data
Aug. 3, 2012 (IT) ............................. TO2012A0698

(51) Int. Cl.
*A61F 13/494* (2006.01)
*A61F 13/551* (2006.01)
(Continued)

(52) U.S. Cl.
CPC ....... *A61F 13/4942* (2013.01); *A61F 13/15747* (2013.01); *A61F 13/15756* (2013.01);
(Continued)

(58) Field of Classification Search
CPC .................... A61F 13/49014; A61F 13/49015; A61F 13/49001; A61F 13/49413; A61F 13/4942; A61F 13/6522; A61F 13/565; A61F 13/62; A61F 13/622; A61F 13/625; A61F 13/627; A61F 2013/49092; A61F 2013/49093; A61F 2013/4944; A61F 2013/586; A61F 2013/587; A61F 2013/588; A61F 13/6275

See application file for complete search history.

(56) References Cited

U.S. PATENT DOCUMENTS

| 4,695,278 A | 9/1987 | Lawson |
| 4,704,116 A | 11/1987 | Enloe |

(Continued)

FOREIGN PATENT DOCUMENTS

| EP | 2289466 A1 | 3/2011 |
| WO | 95/01768 A2 | 1/1995 |

(Continued)

OTHER PUBLICATIONS

International Search Report and Written Opinion dated Mar. 21, 2013 for Application No. PCT/IB2012/056006.

*Primary Examiner* — Lynne Anderson

(74) *Attorney, Agent, or Firm* — Patterson & Sheridan, LLP

(57) ABSTRACT

Pre-fastened and refastenable pant-type absorbent sanitary article, comprising: a central body having two opposite side edges and including: a topsheet having an inner surface, a backsheet, and an absorbent core sandwiched between the topsheet and the backsheet, wherein the topsheet and the backsheet are welded together along a perimeter of the central body, and wherein the central body is folded along a transverse folding line (A) orthogonal to said side edges, at least two side panels extending from respective lateral edges of said central body, each of said side panels having at least one folded portion which extends inwards from the respective side edge and a fastening element of an openable and refastenable fastening device, and at least one strip of sheet material fixed on said inner surface of said topsheet.

4 Claims, 7 Drawing Sheets

(51) Int. Cl.
*A61F 13/15* (2006.01)
*A61F 13/56* (2006.01)
*A61F 13/49* (2006.01)

(52) U.S. Cl.
CPC ..... *A61F13/49466* (2013.01); *A61F 13/55115* (2013.01); *A61F 13/565* (2013.01); *A61F 2013/4944* (2013.01); *A61F 2013/49093* (2013.01); *Y10T 156/1049* (2015.01)

(56) References Cited

U.S. PATENT DOCUMENTS

| | | | |
|---|---|---|---|
| 4,795,454 A | | 1/1989 | Dragoo |
| 4,937,887 A | * | 7/1990 | Schreiner .............. A44B 18/00 2/237 |
| 5,895,382 A | * | 4/1999 | Popp ................. A61F 13/49014 604/385.21 |
| 5,930,875 A | * | 8/1999 | Schreiner .............. A44B 18/00 24/442 |
| 5,993,433 A | * | 11/1999 | St. Louis ............. A61F 13/4942 604/385.27 |
| 6,513,221 B2 | | 2/2003 | Vogt et al. |
| 6,514,187 B2 | | 2/2003 | Coenen et al. |
| 7,322,925 B2 | | 1/2008 | Couillard et al. |
| 7,335,150 B2 | | 2/2008 | Coenen et al. |
| 7,387,148 B2 | | 6/2008 | Vogt et al. |
| 8,216,205 B2 | * | 7/2012 | Suzuki ............. A61F 13/49466 604/385.24 |
| 8,221,378 B2 | | 7/2012 | Popp et al. |
| 9,248,056 B2 | * | 2/2016 | Sablone .................. A61F 13/62 |
| 2012/0184937 A1 | | 7/2012 | Sablone et al. |

FOREIGN PATENT DOCUMENTS

| | | |
|---|---|---|
| WO | 01/87562 A2 | 11/2001 |
| WO | 01/87753 A2 | 11/2001 |
| WO | 2011/104647 A1 | 9/2011 |
| WO | 2012/095739 A1 | 7/2012 |
| WO | 2012/123813 A1 | 9/2012 |

\* cited by examiner

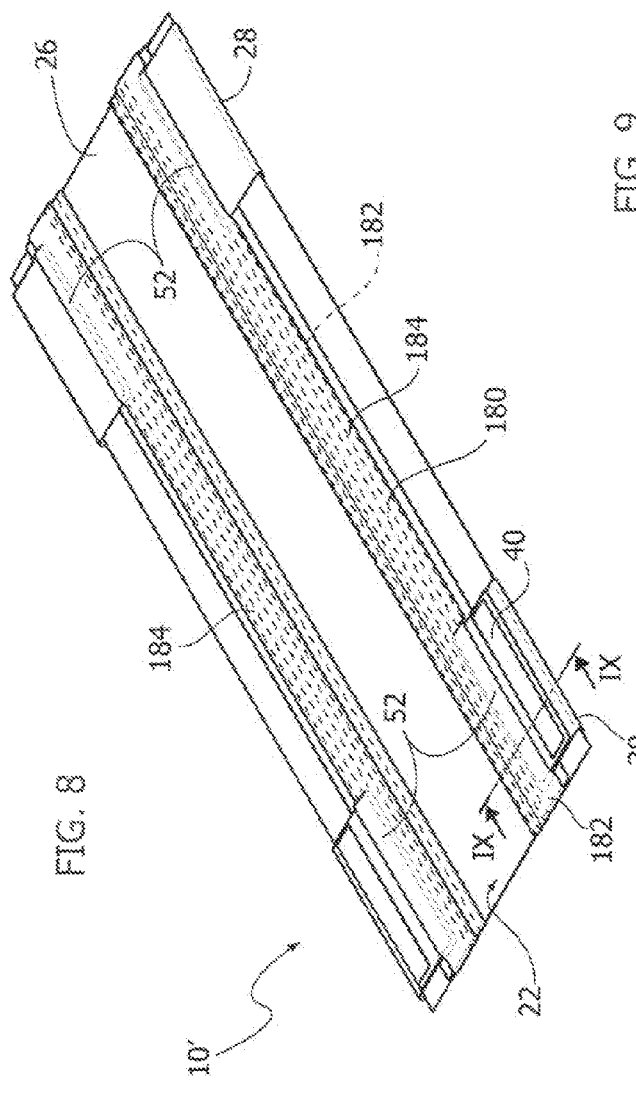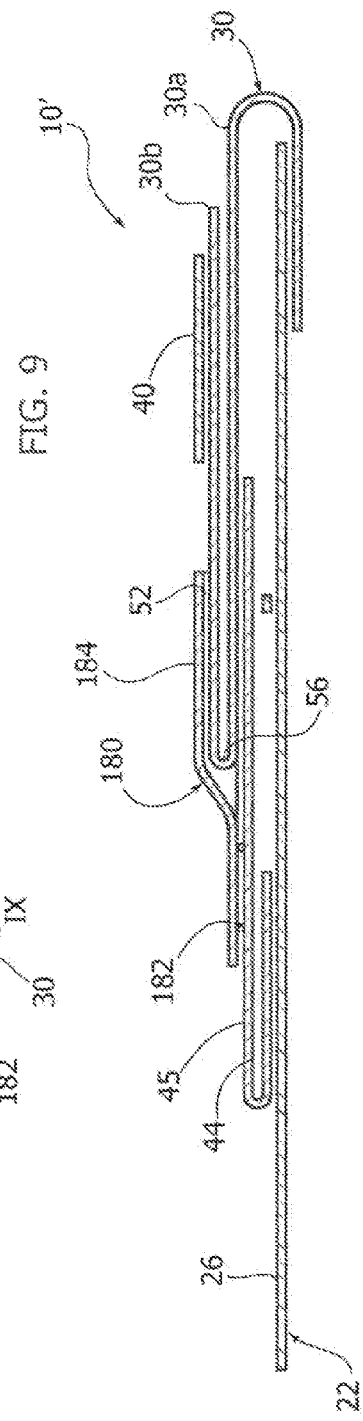

PRE-FASTENED AND REFASTENABLE PANT-TYPE ABSORBENT SANITARY ARTICLE AND METHOD FOR MANUFACTURING THE SAME

TECHNICAL FIELD

The present invention relates to an absorbent sanitary article wearable in pant-form of the pre-fastened and refastenable type, normally referred to as "training pant".

The invention also relates to a method for the manufacturing of such an article.

TECHNOLOGICAL BACKGROUND

In recent years, interest has emerged in diapers of the type commonly referred to as "training-pants". When this product is extracted from the packaging it has a conformation essentially similar to that of a pair of pants. It is worn by sliding it on the legs of the user according to criteria essentially similar to those used for wearing pants.

Training-pants typically include a central body comprising an absorbent core and side panels which extend laterally from the central body so as to complete the pant-type shape of the product. The side panels are fitted with homologous distal edges designed to be connected (pre-fastened) to one another to form fastening regions.

In the most recent products, the pre-fastened fastening regions are openable and closeable, thus allowing the product—sold in a closed pant condition—to be selectively opened on each side.

A technique for the manufacture of pant-type absorbent products envisages the manufacture of discrete flat products that advance in a continuous manner along a direction parallel to the longitudinal direction of the products. The discrete products are then subjected to a folding operation about an axis transverse to the longitudinal axis of the products.

The document U.S. Pat. No. 6,514,187 describes a method and an apparatus for the transverse folding of absorbent products. In the solution described in this document the homologous side panels are maintained separate from each other during the folding operation. The mutual coupling of the side fastenings for closing the product is carried out in a subsequent stage of the manufacture cycle, for example as described in the document U.S. Pat. No. 6,513,221.

Other documents such as U.S. Pat. No. 7,322,925; U.S. Pat. No. 7,335,150, U.S. Pat. No. 7,387,148, EP-A-1289465, EP-A-2289466, EP-A-1284700 describe methods and equipment that can be applied for the manufacture of absorbent products with refastenable side fastenings.

A known solution envisages the inward folding of the side panels, arranged with respective fastening elements facing each other. In this way, when the article is folded transversely, the opposing fastening elements are pressed against each other so as to provide the pre-fastened configuration of the absorbent article.

The document U.S. Pat. No. 8,221,378 describes a solution wherein the folded portions of the side panels are held by temporary releasable welds, having a peel strength less than the peel strength of the refastenable fastening elements of the side panels.

This solution suffers from curious drawbacks. Indeed, the temporary welding that retains the folded portions of the side panels limits the choice of materials usable for the side panels to easily-weldable materials that are compatible with each other. The temporary welding may also ruin the material and produce lacerations in the case in which it has a peel strength greater than the peel strength between the refastenable fastening elements of the side panels. In the case in which the temporary welding has too weak a peel strength, the temporary connection between the folded portions of the side panels could open during the manufacturing method, causing release of the side panels and the non-fastening of the side panels during the transverse folding of the articles.

SUMMARY OF THE INVENTION

The object of the present invention is to provide a solution in order to overcome the drawbacks of the prior art.

According to the present invention, this object is achieved by an absorbent sanitary article and a method for its manufacture having the characteristics forming the subject of the claims included.

The claims form an integral part of the teaching provided herein relation to the invention.

BRIEF DESCRIPTION OF THE DRAWINGS

The present invention will now be described in detail with reference to the attached drawings, provided purely by way of non-limiting example, wherein:

FIG. 8 is a schematic perspective view of a second embodiment of a pant-type absorbent sanitary article according to the invention in its extended configuration and with the side panels folded, and FIG. 9 is a cross section along the line IX-IX of FIG. 8.

DETAILED DESCRIPTION

In the following description, various specific details are illustrated, aimed at a thorough understanding of the embodiments. The embodiments can be implemented without one or more of the specific details, or with other methods, components, materials, etc. In other cases, structures, materials, or known operations are not shown or described in detail to avoid obscuring the various aspects of the embodiments.

The reference to "one embodiment" within the framework of this description is to indicate that a particular configuration, structure or characteristic described in relation to the embodiment is included in at least one embodiment. Therefore, phrases such as "in one embodiment" that may be present in different points of this description, are not necessarily referring to the same embodiment. Furthermore, particular conformations, structures or characteristics may be combined in an appropriate way in one or more embodiments.

The references used herein are for convenience only and therefore do not define the scope or protection or the scope of the embodiments.

Figure 1:
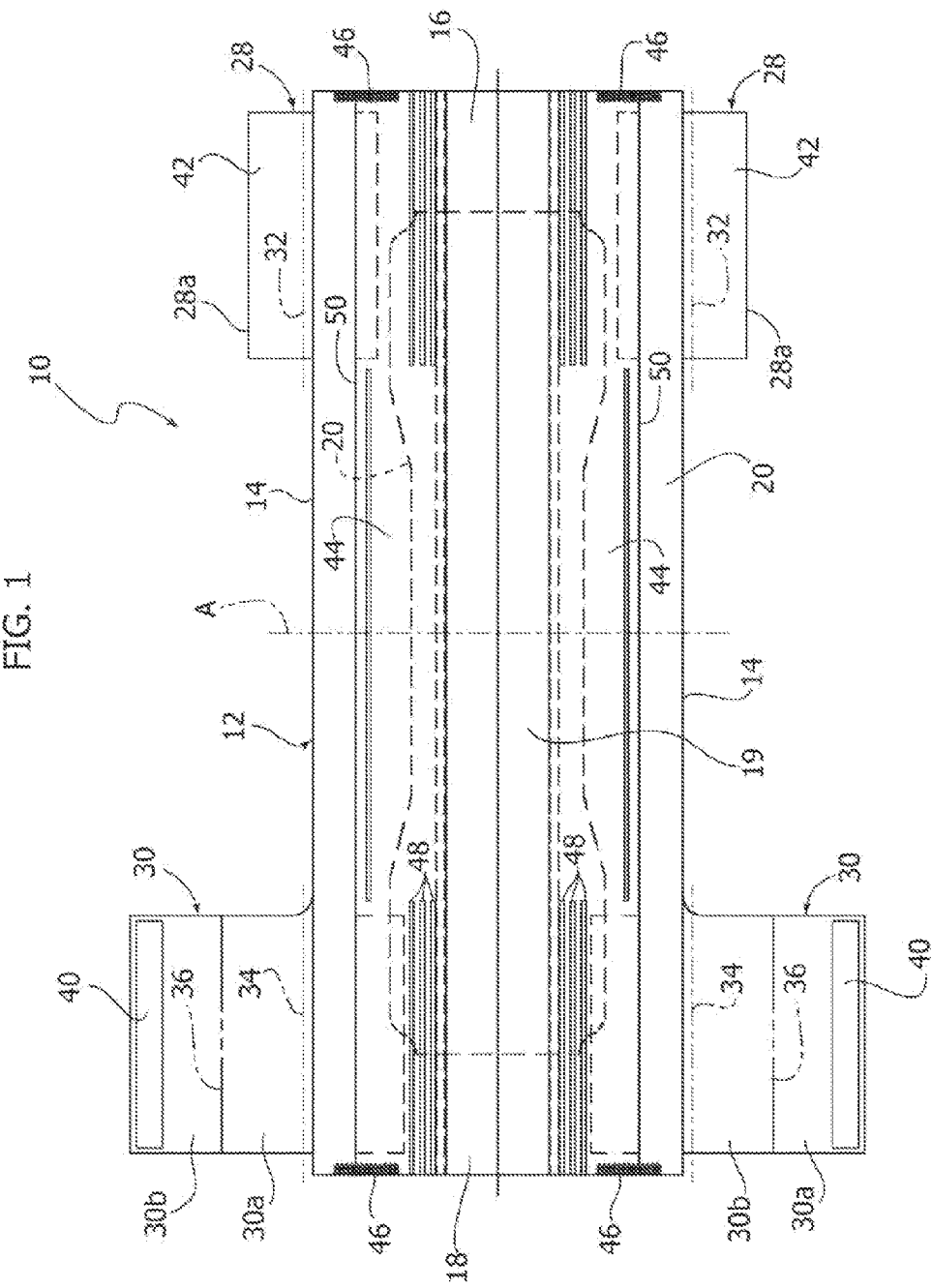
FIG. 1 is a plan view of a first embodiment of a pant-type sanitary absorbent article according to the invention in its extended configuration.
Figure 2:
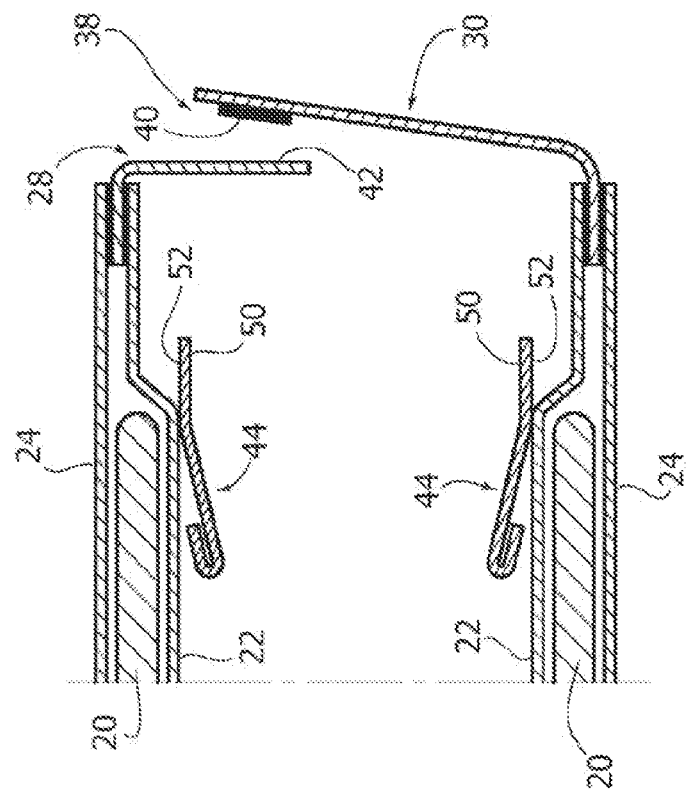
FIG. 2 is a cross-section of a lateral zone of the absorbent product of FIG. 1 in a folded configuration.
Figure 3:
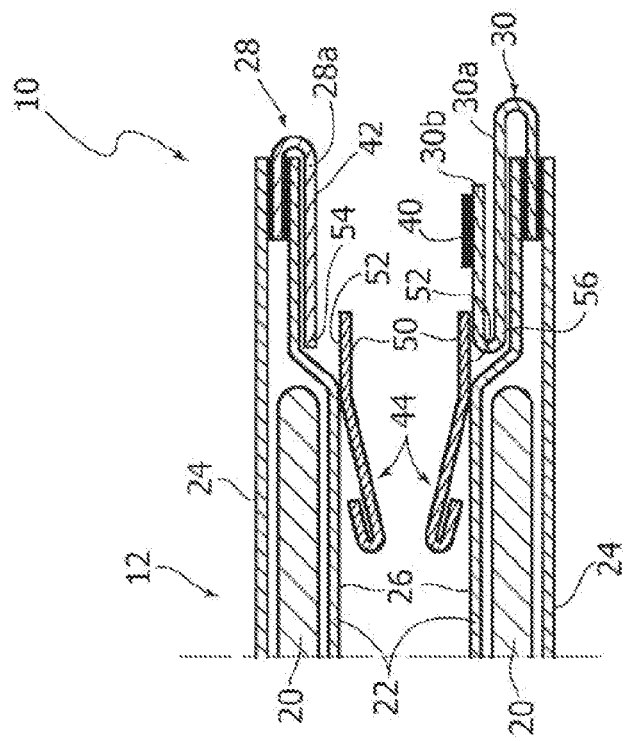
FIG. 3 is a cross section similar to FIG. 1 illustrating the side panels in the open configuration.

With reference to FIGS. 1-3, 10 indicates an absorbent sanitary article wearable in pant-form. FIG. 1 shows the sanitary article 10 in an extended position, i.e. before being folded around its central transverse axis A to obtain the folded configuration in which the article 10 is packaged and sold. FIGS. 2 and 3 show side portions of article 10 in the folded configuration. Article 10 comprises a central body 11 having two opposite side edges 14, a front waist portion 16, a back waist portion 18 and a crotch portion 19 located between the front waist portion 16 and the back waist portion 18.

With reference to FIGS. 2 and 3, according to conventional methods in the field, the central body 12 comprises an absorbent core 20 which is enclosed like a sandwich between a topsheet 22 and a backsheet 24. The topsheet 22 is at least partially permeable to bodily fluids and has an inner surface 26 intended to face towards the user's body. The backsheet 24 is impervious to liquids and is intended to face towards the exterior, or rather towards the user's clothing.

In one embodiment, the article 10 comprises two front side panels 28 add two rear side panels 30 which extend from respective side edges 14 of the central body 12. The front and rear side panels 28, 30 may be permanently attached to the respective front area rear waist portions 16, 18 of the central body 12 or may be part of the lateral extensions of the topsheet 22 or the backsheet 24 or both. Furthermore, said lateral panels 28, 30 may or may not present characteristics of elasticity in the transverse direction.

It is underlined that the connotations "front" and "rear" are used herein only to distinguish the two ends from each other, and therefore has no specific relevance regarding the manner in which the product is finally worn.

In one embodiment, in the configuration in which one article 10 is produced and sold, the front side panels 28 have respective first folded portions 28a (FIG. 2) folded inwardly along their respective fold lines 32 (FIG. 1).

In one embodiment, the rear side panels 30 are folded according to an essentially S-shaped configuration and have respective first folded portions 30a, folded inwardly along respective first fold lines 34. The rear side panels 30 also have respective second folded portions 30b, folded along second fold lines 36 on respective first folded portions 30a.

The front and rear side panels 28, 30 are connected together by means of an openable and refastenable fastening device 38. Each openable and refastenable fastening device 38 comprises at least one fastening element 40 fixed on one of the side panels 28, 30 and cooperating with a facing surface 42 of the other side panel 28, 30 or with a complementary fastening element fixed on the other side panel 28, 30.

Each fastening element may comprise a single section or multiple sections of fastening elements. The fastening elements may comprise any refastenable fastening suitable fox absorbent articles, such as adhesive fastenings, mechanical fastenings or similar.

In one embodiment, each openable and refastenable fastening device 38 comprises a fastening element 40 with microhooks fixed to the rear side panel 30 and which engages a surface 42 of the front side panel 28 in a separable way. In this embodiment, the surface 42 of the side panel 28 is constituted of a material (e.g. non-woven) suitable for coupling with the microhook fastening element 40 in an openable and refastenable manner.

The complementary fastening elements 40, 42 of each openable and refastenable fastening device 38 are located on respective opposite surfaces of the respective side panels 28, 30, and are facing each other, as represented in FIG. 2. In this way, when the absorbent article 10 is folded in two along the transverse folding line A, the fastening elements 40, 42 will be situated in front of each other, and therefore able to connect to each other by means of a simple contact pressure.

Still with reference to FIGS. 1-3, the central body 12 of article 10 comprises two barrier leg cuffs 44 fixed to the inner surface 26 of the topsheet 22. The barrier leg cuffs 44 are configured to provide a barrier to the transverse flow of body exudates. The barrier leg cuffs 44 are usually formed of elastic or elasticized material, and extend in the longitudinal direction, parallel to the respective side edges 14 of the central body 12. The barrier leg cuffs 44 are secured to the topsheet 26 by means of welding ends 46 and via longitudinal welding lines 48 (FIG. 1). In one embodiment, the longitudinal welds 48 only extend at the front waist portion 16 and the back waist portion 18, whereby the barrier leg cuffs 44 are detached from the topsheet 44 in the crotch area 19. The barrier leg cuffs 44 apply an elastic force between the front waist portion 16 and the back waist portion 18 so that the sanitary article 10 tends to assume the characteristic pant-shape. The barrier leg cuffs 44 are positioned adjacent to respective side edges 14 of the central body 12 and can extend longitudinally along the entire length or just a part of the length of the central body 12.

The construction methods and embodiments of the barrier leg cuffs 44 are generally well known to those skilled in the art and are described in documents U.S. Pat. No. 4,695,278, U.S. Pat. No. 4,704,116 and U.S. Pat. No. 4,795,454.

With reference to FIGS. 2 and 3, each barrier leg cuff 44 has an outer side portion 50 detached from the surface 26 of the topsheet 22, so as to form a laterally outwards-opening pocket 52. The pocket 52 is configured to receive and retain a respective inner edge top 54, 56 of she folded portions 28a, 30a, 30b of the respective side panels 28, 30.

In one embodiment, each barrier leg cuff 44 retains a front side panel 28 and a rear side panel 30 in a folded position. The article 10 could comprise a single pair of front 28 or rear 30 side panels. In this case, each barrier leg cuff 44 would only retain one side panel 28 or 30 in a folded configuration.

The pockets 52 formed by the laterally prospecting portions 50 of the barrier leg cuffs 44 retain the side panels 28, 30 in a folded position and avoid the need to provide temporary welds on the folded portions 28a, 30a, 30b of the side panels designed to break at the act of opening of the sanitary article 10.

As is illustrated in FIG. 2, the pockets 52 hold the side panels 28, 30 in a folded position during the method of manufacturing of the sanitary article 10 so as to allow the mutual engagement between the fastening elements 40, 42 as a result of a contact pressure. On the other hand, as shown in FIG. 3, the pockets 52 release the side panels 28, 30, without resistance, at the moment of opening of the sanitary article 10.

In FIGS. 8 and 9, a further preferred embodiment of the absorbent sanitary article 10 according to the present invention is illustrated. The elements corresponding to those previously described are indicated by the same reference numerals.

In this further embodiment, the pockets 52 are formed by directly laminating at least one sheet material 180 on the topsheet 22. In particular, two strips of sheet material 180 may be laminated onto the absorbent article 10, which can be connected directly to the inner surface 26 of the topsheet 22. In the case wherein elasticized barrier leg cuffs 44 are present, the strips of sheet material 180 may be indirectly connected to the inner surface 26 of the topsheet 22 through said barrier leg cuffs 44. In this case, the two strips of sheet material 180 may be laminated on the upper surface 45 of the barrier leg cuffs 44 which in use is typically directed toward the user's body.

The sheet material 180 has an outer side portion 184 partially detached from the surface 26 of the topsheet 22, or, if the barrier leg cuffs 44 are present, as in the embodiment illustrated in FIGS. 8 and 9, from the upper surface 45 of the respective cuff 44, so as to form laterally outwards-opening pockets 52. The pockets 52 are produced by combining the outer side portion 184 of the sheet material 180 respectively to the upper surface 26 of the topsheet 22 or the barrier leg cuff 44 in a discontinuous manner.

In the further embodiment shown in FIGS. 8 and 9, the folded portions 28a, 30a, 30b of the respective side panels 28, 30 are held in the folded position by the pockets 52 which are formed by fixing the two strips of sheet material 180 by means of welds 182 on the respective barrier leg cuffs 44 in a discontinuous manner. The welds 182 may be made using any method normally used in the field (glues, ultrasound, thermal, etc.). The composition of the materials of the absorbent product 10 is not described in detail since it is beyond the scope of the present invention. The absorbent product 10 may be constructed with any form, components or materials known in the field.

Figure 4:
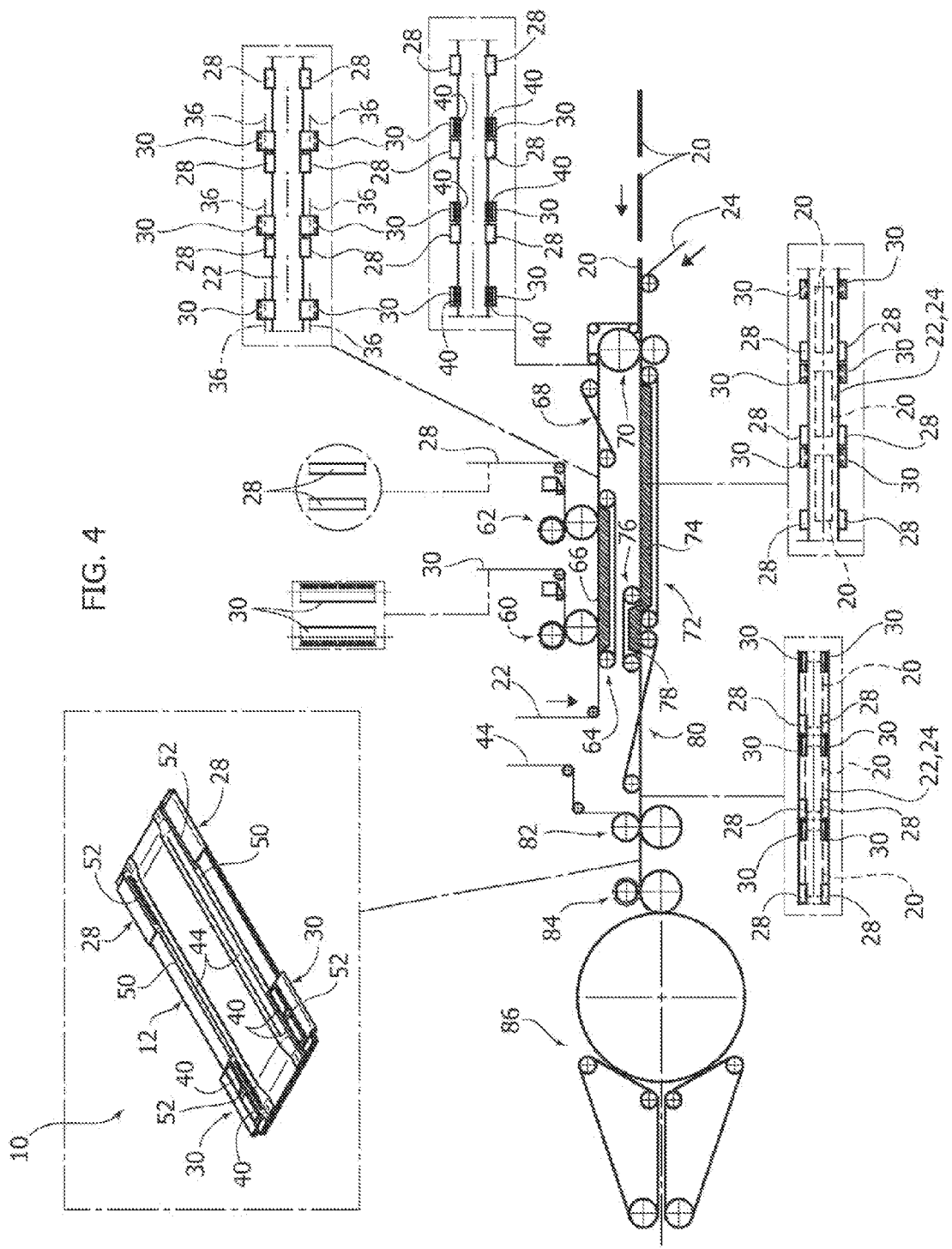
FIG. 4 is a schematic view illustrating a method for the manufacture of sanitary absorbent articles according to the present invention.
Figure 5:
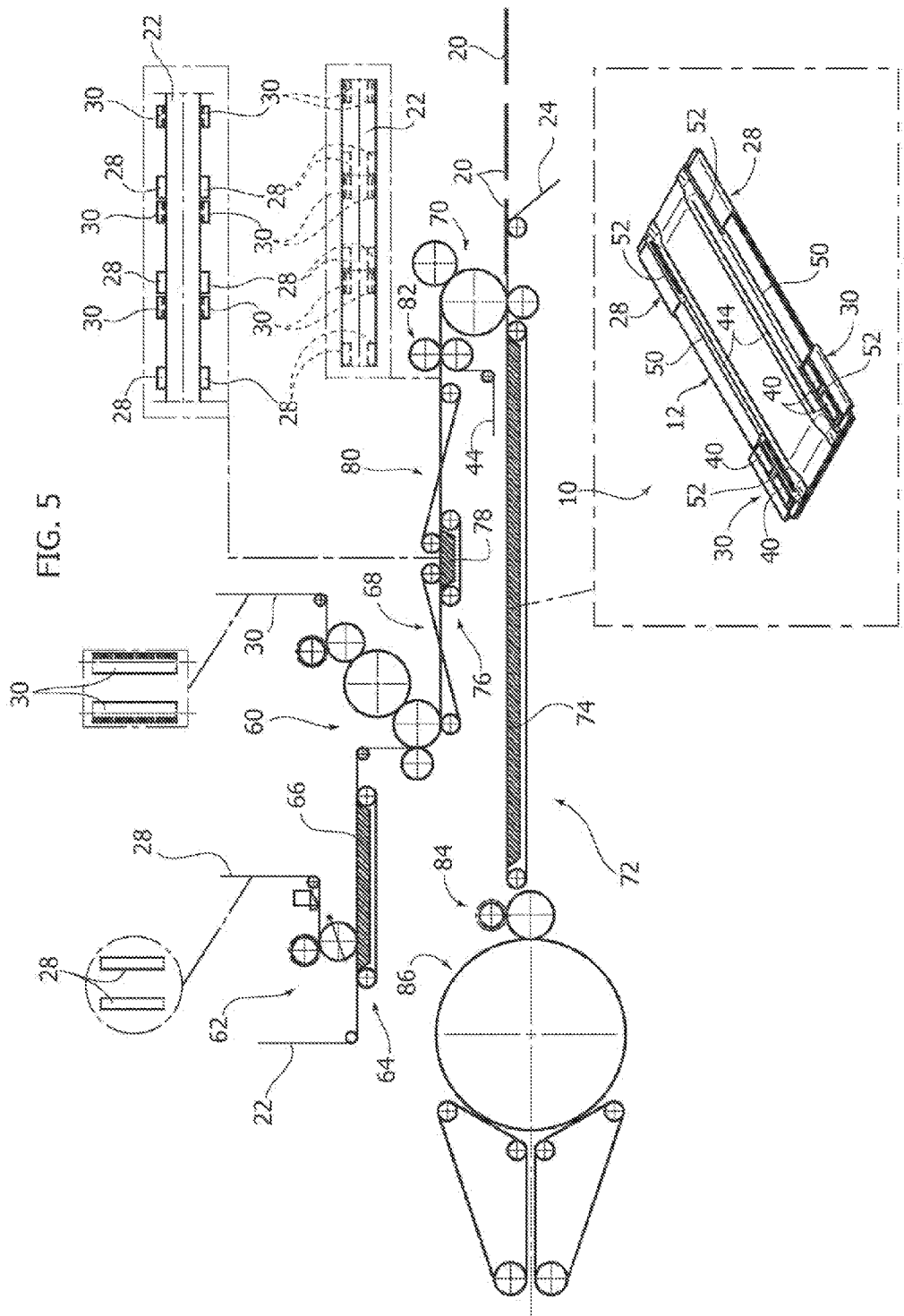
FIG. 5 is a schematic view illustrating a second embodiment of the method according to the invention.
Figure 7:
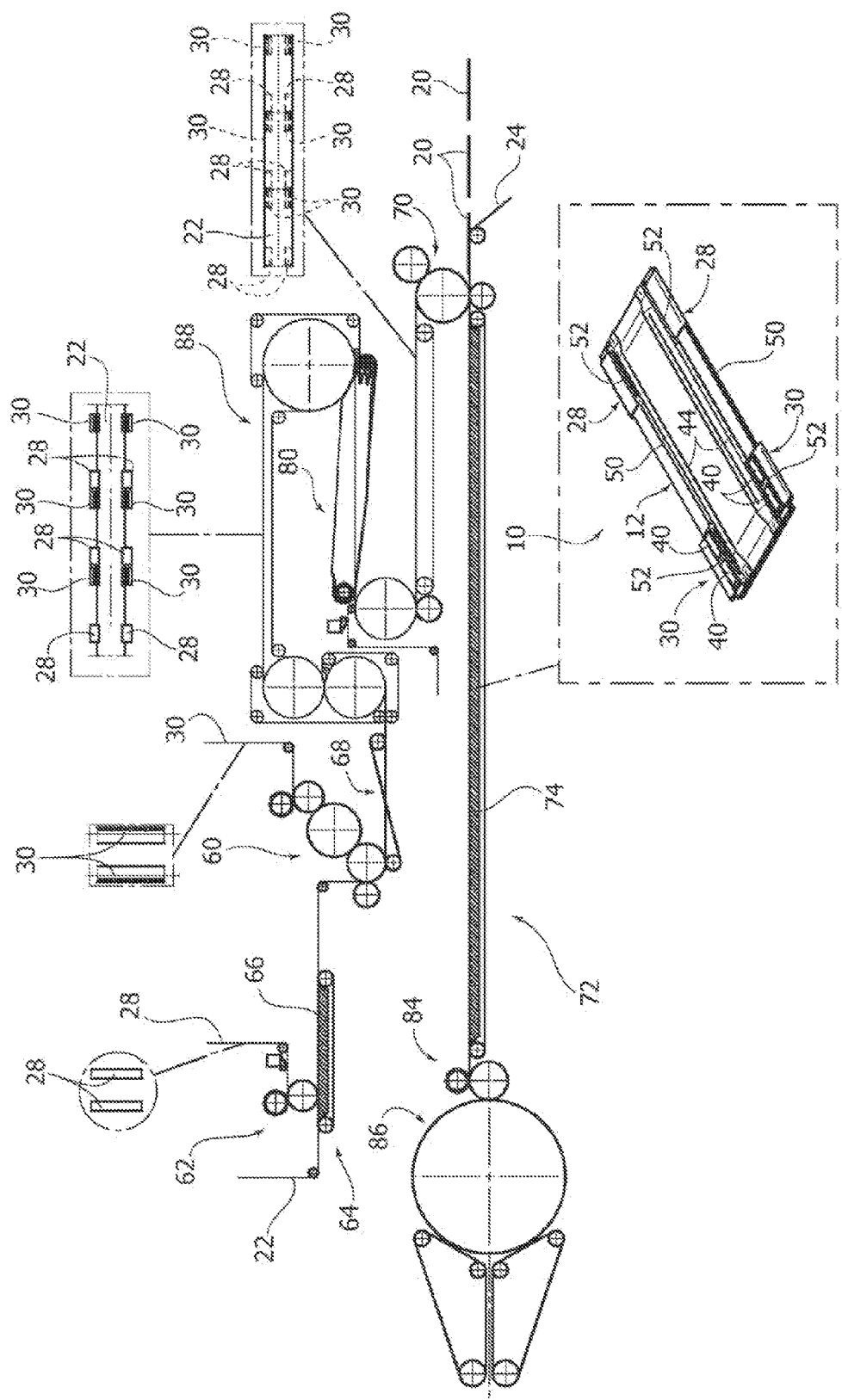
FIG. 7 is a schematic view illustrating a third embodiment of the method according to the invention.

In FIGS. 4, 5 and 7 three variants of a method for the manufacture of an absorbent sanitary article 10 at tae type previously described are illustrated. In all the variants, the method for manufacturing the articles 10 envisages the formation of a continuous composite sheet which advances in a longitudinal direction. The composite sheet is formed by a continuous succession of blanks of articles 10 aligned with each other in the longitudinal direction. In the continuous composite sheet, the articles 10 are oriented parallel to the direction of movement, or the belt. The continuous composite sheet is then out in the transverse direction to form discrete articles 10. This manufacturing technique is known in the field of absorbent products by the term "machine direction".

In FIGS. 4, 5 and 7, inside the boxes or circles surrounded by dashed and dotted lines, enlarged details are shown of the composite sheet corresponding to the steps of the method indicated by the corresponding dashed and dotted lines.

With reference to FIG. 4, a continuous sheet forming the topsheet 22 is advanced along the longitudinal direction. A first applicator 60 applies, on the upper surface of the moving sheet 22, pairs or rear side panels 30 in an extended position and spaced from each other in the longitudinal direction. On the rear side panels 30, fastening elements 40 have previously been applied. A second applicator 62 applies, on the upper surface of the moving sheet 22, pairs of front side panels 28 in an extended position and spaced from each other in the longitudinal direction. Between the applicators 60 and 62 the sheet 22 is supported by a first conveyor 64 with suction box 66.

A first longitudinal folding device 68 folds the second folded portions 30b of the rear side parcels 30 about the second fold lines 36. The first longitudinal folding device 68 may be of the type described in the document WO2011/104647.

The first composite sheet including the topsheet 22 and the side panels 28, 30 is supplied by a first welding unit 70.

A continuous sheet forming the backsheet 24 is advanced in a direction opposite to the direction of advancement of the topsheet 22. On the upper surface of the backsheet 24 absorbent cores 20, spaced apart in the longitudinal direction, are applied. The second composite sheet including the backsheet 23 and the absorbent cores 20 is supplied to the first welding unit 70.

The first welding unit 70 reverses the advancing direction of the first composite sheet including the topsheet 22 and the side panels 28, 30 and applies the first composite sheet onto the upper surface of the second composite sheet including the backsheet 24 and absorbent cores 20. At the same time, the first welding unit 70 welds together the topsheet 22 and the backsheet 24 in the longitudinal direction. This welding also welds the side panels 20, 30 to the topsheet 22 and the backsheet 24.

Downstream of the first welding unit 70 the sheet advances by means of a second conveyor 72 with suction box 74. At the output of the second conveyor 72, a third conveyor 76, with suction box 78, is provided, opposite to the second conveyor 72.

Downstream of the third conveyor 76 a second longitudinal folding device 80 is arranged which carries out the folding of the first folded portions 28a of the first front, side panels 28 about the folding line 32 and the folding of the first folded portions 30a of the rear side panels 30 about the folding lines 34. The second longitudinal folding device 80 may also be of the type described in the document WO2011/104647. At the output of the second longitudinal folding device 80, the side panels 28, 30 are folded on the upper surface of the topsheet 22.

Downstream, of the second folding longitudinal side 80, the carrier leg cuffs 44 are supplied to the upper surface of the topsheet 22 in the form of two continuous strips. The barrier leg cuffs 44 are applied to the topsheet 22 so that the outer side edges 50 of the barrier leg cuffs 44 partially cover the inner edges of the folded side panels 28, 30.

A second welding unit 82 welds the barrier leg cuffs 44 to the topsheet 22. The welding is carried out leaving the outer side edge 50 of the barrier leg cuffs 44 detached from the upper surface of the topsheet 22, so as to form the pockets 52 which retain the side panels 28, 30 in a folded position.

Downstream of the welding unit 82 a continuous chain of blanks of absorbent articles 10 is obtained. The continuous chain of blanks is cut in the transverse direction by means of a transverse cutting unit 84 obtaining a continuous succession of discrete absorbent articles 10 in extended form.

The discrete articles 10, initially in the extended form, are then folded about respective transverse folding lines A. In FIG. 4 the numeral 86 indicates an apparatus for the transverse folding of discrete products 10 initially in the extended condition. The transverse folding apparatus 86 may be of the type described in the international patent application no. PCT/IB2012/000520.

As a result of the transverse folding, the front and rear waist portions 16, 18 of each article 10 are superposed on each ether. After folding, the fastening elements 40, 42 are located an a position facing each other and are susceptible to being joined to each other under the action of a contact pressure.

It should be appreciated that as a result of folding about the transverse axis A, and as a result of the mutual connection between the fastening elements 40, 42 the product 10 assumes the conformation of a garment wearable in pant-form.

FIG. 5 shows a variant of the method according to the invention. The elements corresponding to those previously described are indicated by the same reference numerals.

With reference to FIG. 5, the side panels 28, 30 in an extended position are applied to the moving topsheet 22, as in the method previously described. After application of the side panels 28, 30 in the extended position, the side panels are folded by means of the first longitudinal folding device 68 and the second longitudinal folding device 80.

After folding of the side panels, the barrier leg cuffs 44 are applied and welded on the surface facing towards the bottom of the topsheet 22. The application and welding of the barrier leg cuffs 44 is as described previously, with the formation of the pockets 52 which retain the side panels 28, 30 in a folded position.

Then, the first composite sheet including the topsheet 22, the folded side panels 28, 30 and the barrier leg cuffs 44 is supplied to the welding unit 70 which overturns the first composite sheet.

The second composite sheet formed by the backsheet 24 and the absorbent cores 20 is also fed to the welding unit 70.

The welding unit 70 applies and welds the first composite sheet including the topsheet 22, the folded side panels 28, 30 and the barrier leg cuffs 44 onto the second composite sheet including the backsheet 24 and absorbent cores 20.

At the output of the welding unit 70 a continuous chain of blanks of articles is obtained, which is transversely cut by the transverse cutting unit 84. The individual articles in an extended position are then folded in the transverse direction by the transverse folding apparatus 86, as previously described.

Figure 6:
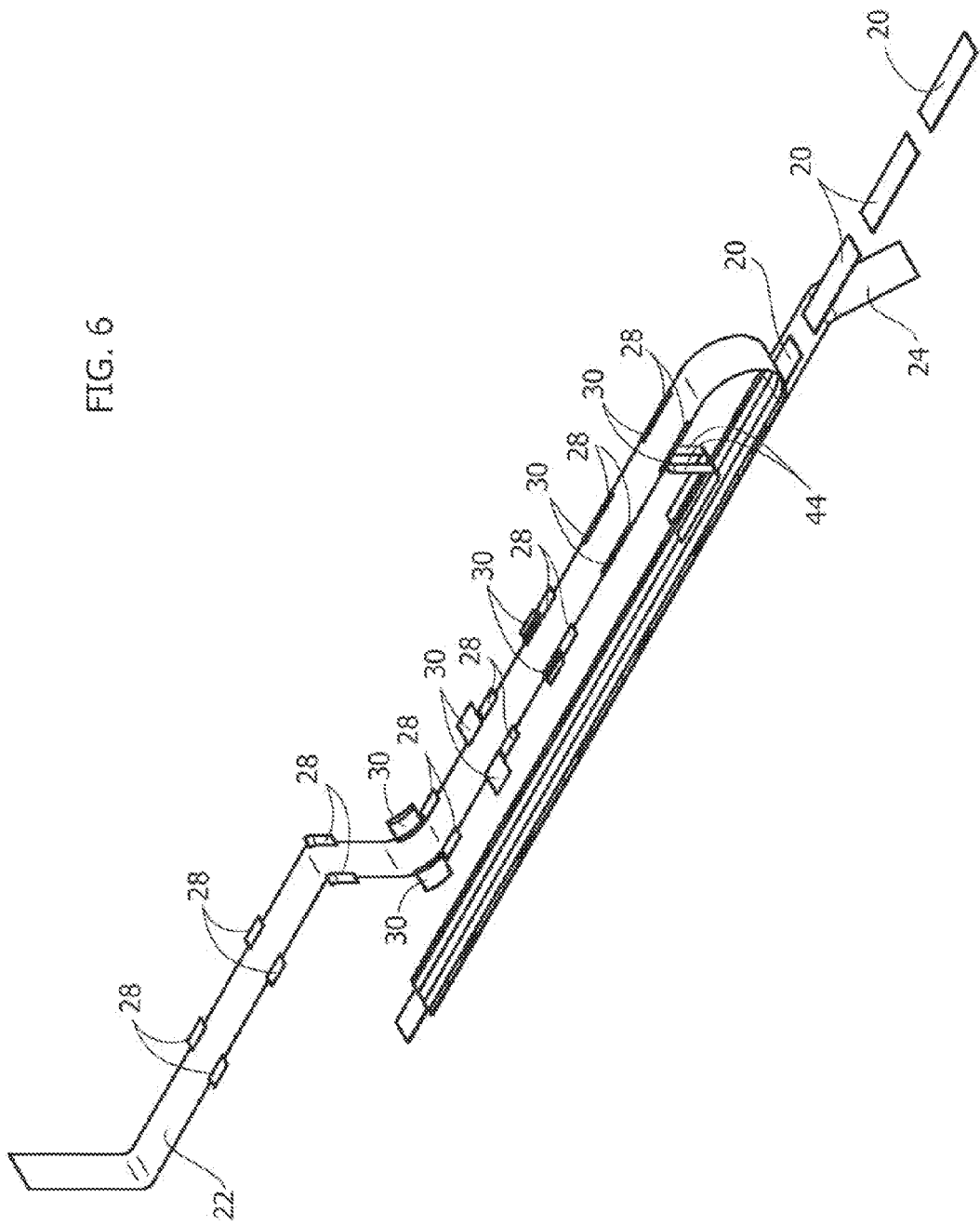
FIG. 6 is a schematic perspective view illustrating some steps of the method of FIG. 5.

FIG. 6 schematically shows in a perspective view the steps of: folding of the side panels 28, 30, application of the barrier leg cuffs 44, overturning of the first composite fabric and application of the first composite sheet onto the second composite sheet.

FIG. 7 shows a second variant of the method according to the invention. The variant of FIG. 7 envisages, as in the method of FIG. 5, the application of the side panels 28, 30 in an extended position on the moving topsheet 22, the folding of the side panels 28, 30 by means of the first longitudinal folding devices 68 and the second longitudinal folding device 80 and the application of the barrier leg cuffs 44 on the topsheet 22. The variant of FIG. 7 differs from the method of FIG. 5 in the fact that between the first longitudinal folding device 68 and the second longitudinal folding device 80, a transfer belt 88 is arranged that does not use suction boxes.

It will be apparent to experts in the field that the same methods described and illustrated schematically in FIGS. 4, 5 and 7 may be advantageously used for the manufacture of the absorbent article 10 of the embodiment sheen in FIGS. 8 and 9, by simply providing, at the input of the applicators 60 and 62—responsible for applying respective rear 30 and front 20 panels—one topsheet 22 which may already be equipped with barrier leg cuffs 44, and applying the two sheet materials 180 immediately after having carried out the folding operations of said rear 30 and front 28 panels, in such a way that the second welding unit 82 can combine the two strips of sheet material 180 onto the inner surface 26 of the topsheet 22 or, if the barrier leg cuffs 44 are present, on the upper surfaces 45 of the respective barrier leg cuffs 44, producing joint (or weld) areas 182, as well illustrated in FIGS. 8 and 9. The weld 182 is produced by combining each sheet material 180 in a discontinuous manner, leaving the outer side edge 184 of each strip of sheet material 180 detached from the inner surface 26 of the topsheet 22 or, if present, from the upper surfaces 45 of the respective barrier leg cuff 44, so as to form the pockets 52 which retain the side panels 28, 30, in a folded position as represented in FIGS. 8 and 9.

The method can also be easily modified by experts so as to apply a single sheet material 180 to form the packets 52.

Of course, without prejudice to the principle of the invention, the details of construction and the embodiments may be varied widely with respect to those described and illustrated without thereby departing from the scope of the invention as defined by the claims that follow.

The invention claimed is:

1. Pant-type pre-fastened and refastenable absorbent sanitary article, comprising:
    a central body having two opposite side edges and including a topsheet having an inner surface, a backsheet, and an absorbent core sandwiched between the topsheet and the backsheet, wherein the topsheet and the backsheet are welded together along a perimeter of the central body, and wherein the central body is folded along a transverse folding line (A) orthogonal to said side edges; and
    at least two side panels extending from respective side edges of said central body, each of said side panels having at least one folded portion that extends inwardly from the respective side edge and a fastening element of an openable and refastenable fastening device,
    a pair of barrier leg cuffs fixed on said inner surface of said topsheet,
    a pair of strips of sheet material fixed on an upper surface of respective barrier leg cuffs, wherein said strips of sheet material have respective outer side portions detached from the upper surface of the respective cuff and forming laterally outwards-opening pockets that receive and retain the respective inner edges of the respective folded portions of the side panels.

2. Article according to claim 1, further comprising a first pair of side panels having one folded portion and a second pair of side panels having a first and a second folded portion arranged in an S-shaped configuration, an openable and refastenable fastening device being arranged between mutually facing surfaces of said folded portions of the first and second pair of side panels.

3. Article according to claim 2, wherein said openable and refastenable fastening device comprises a microhook fastening element fixed to one of said folded portions and cooperating with a facing surface of the complementary folded portion or with a fastening element fixed on the folded complementary portion.

4. Method for manufacturing a pre-fastened and refastenable pant-type absorbent sanitary article, comprising the steps of:
    advancing a continuous topsheet along a longitudinal direction;
    applying pairs of side panels to said moving topsheet in spaced apart positions in the longitudinal direction;
    folding said side panels along folding lines parallel to the longitudinal direction of said topsheet;
    applying barrier leg cuffs to said topsheet in the form of two continuous strips; and
    fixing a pair of continuous strips of sheet material on an upper surface of said barrier leg cuffs, wherein said strips of sheet material have respective outer side portions detached from the upper surface of the respective cuff and forming laterally outwards-opening pockets that receive and retain the respective inner edges of the respective folded portions of the side panels.

* * * * *